(12) United States Patent
Chatellier et al.

(10) Patent No.: US 6,684,703 B2
(45) Date of Patent: Feb. 3, 2004

(54) METHOD FOR MEASURING ADHERENCE OF A COATING ON A SUBSTRATE

(75) Inventors: Jean-Yves François Roger Chatellier, Arcueil (FR); Daniel Sébastien Ramahefasolo, Echarcon (FR)

(73) Assignee: Snecma Moteurs, Paris (FR)

( * ) Notice: Subject to any disclaimer, the term of this patent is extended or adjusted under 35 U.S.C. 154(b) by 0 days.

(21) Appl. No.: 09/926,435

(22) PCT Filed: Mar. 1, 2001

(86) PCT No.: PCT/FR01/00607
§ 371 (c)(1),
(2), (4) Date: Nov. 2, 2001

(87) PCT Pub. No.: WO01/65229
PCT Pub. Date: Sep. 7, 2001

(65) Prior Publication Data
US 2002/0162395 A1 Nov. 7, 2002

(30) Foreign Application Priority Data
Mar. 2, 2000 (FR) .............................................. 00 02669

(51) Int. Cl.$^7$ ................................................. G01N 9/24
(52) U.S. Cl. .............................. 73/600; 73/599; 73/602; 73/646
(58) Field of Search .......................... 73/646, 579, 600, 73/599, 602, 627, 629

(56) References Cited

U.S. PATENT DOCUMENTS

| 4,541,287 A | | 9/1985 | Roper ........................... 73/827 |
| 5,349,860 A | * | 9/1994 | Nakano et al. ................ 73/597 |
| 5,372,042 A | * | 12/1994 | Jarman et al. ................. 73/588 |
| 5,469,736 A | * | 11/1995 | Moake ..................... 73/152.58 |
| 5,559,292 A | * | 9/1996 | Hull et al. ..................... 73/597 |
| 5,627,320 A | * | 5/1997 | Moore .......................... 73/606 |
| 5,631,425 A | * | 5/1997 | Wang et al. .................. 73/606 |
| 5,641,906 A | * | 6/1997 | Moore .......................... 73/614 |
| 5,663,502 A | | 9/1997 | Nagashima et al. ........... 73/599 |
| 5,929,315 A | * | 7/1999 | Dunegan ..................... 73/1.82 |
| 6,089,095 A | * | 7/2000 | Yang et al. ................... 73/600 |
| 6,200,266 B1 | * | 3/2001 | Shokrollahi et al. ......... 600/438 |
| 6,374,675 B1 | * | 4/2002 | DePetrillo .................... 73/610 |

\* cited by examiner

*Primary Examiner*—Hezron Williams
*Assistant Examiner*—Jacques Saint-Surin
(74) *Attorney, Agent, or Firm*—Oblon, Spivak, McClelland, Maier & Neustadt, P.C.

(57) ABSTRACT

A process for measuring the bond of a coating on a substrate. Ultrasound echoes through the substrate of a test piece are collected and their amplitudes are measured, their decay being a function of the bond of a coating deposited on the opposite face of the substrate. Preliminary tests on calibration test pieces give a correlation function so that it is unnecessary to carry out expensive and uncertain mechanical tests on the test pieces.

12 Claims, 2 Drawing Sheets

METHOD FOR MEASURING ADHERENCE OF A COATING ON A SUBSTRATE

DESCRIPTION

This invention relates to a process for measuring the bond of a coating on a substrate.

The bond of a coating on a substrate may be evaluated by gluing the free faces of the assembly obtained on both sides of the junction interface, to plane surfaces with jaw ends that are drawn in opposite directions on a tensile testing machine. The bond measurement then consists of making a direct mechanical measurement of the force necessary to break the junction and tear the coating off the substrate. However, very wide dispersions of the measured failure forces are always observed for test pieces made in a similar manner, which proves that uncertainties are introduced in the operating method, that are so large that in practice these tests are valueless. It is probable that gluing is responsible for defects in the uniformity with which the tension force is transmitted through the assembly, but it is impossible to compensate for this even when taking the greatest care with the preparation.

This patent proposes an indirect method of measuring this resistance to tearing the coating off the substrate, making use of ultrasound measurements. In its most general form, the invention relates to a process for measuring the bond of a coating on a substrate, characterized in that it consists of sending ultrasounds into the substrate and to the coating, picking up a series of echoes resulting from the ever increasing number of ultrasound reflections on the faces of the substrate with an interface between the substrate and the coating, evaluating an echo attenuation coefficient using a function to determine the decay of echo amplitudes as a function of the number of echo reflections, and deducing the said bond of a correlation function estimated in advance using calibration test pieces, using attenuation coefficients and values of coating bond obtained by mechanical tests on calibration test pieces.

Figure 1:
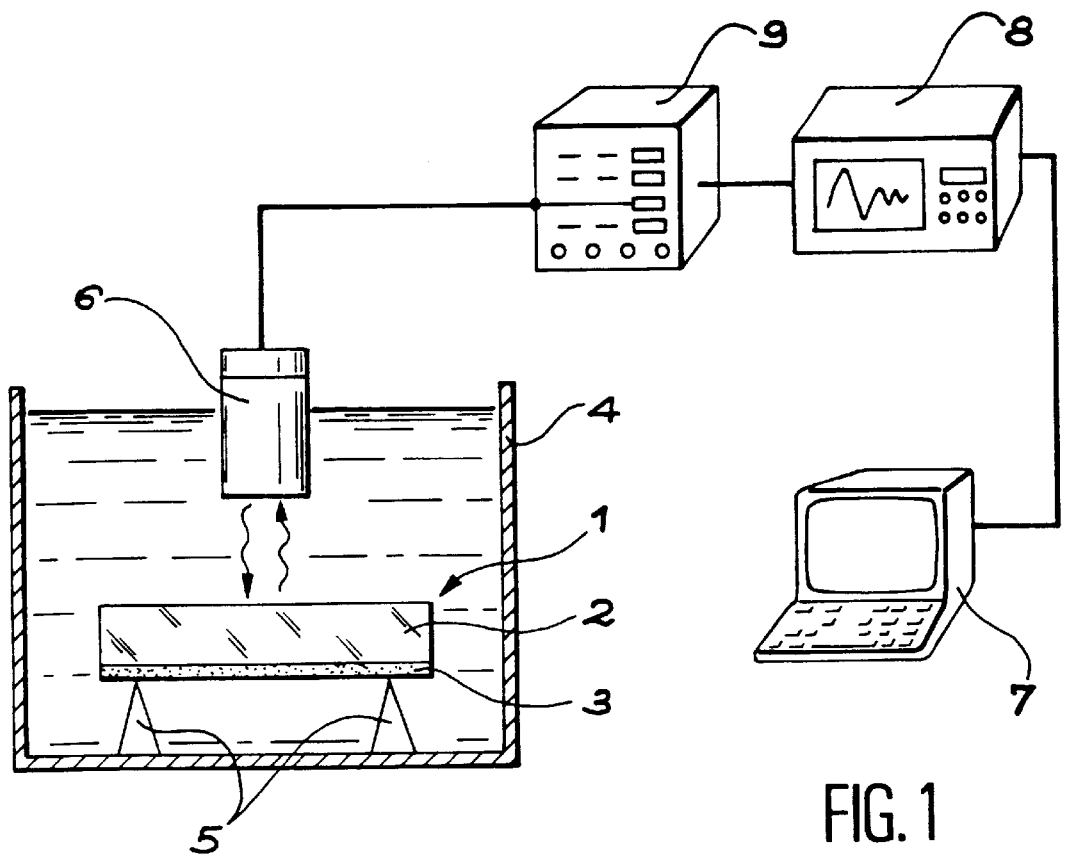
Figure 2:
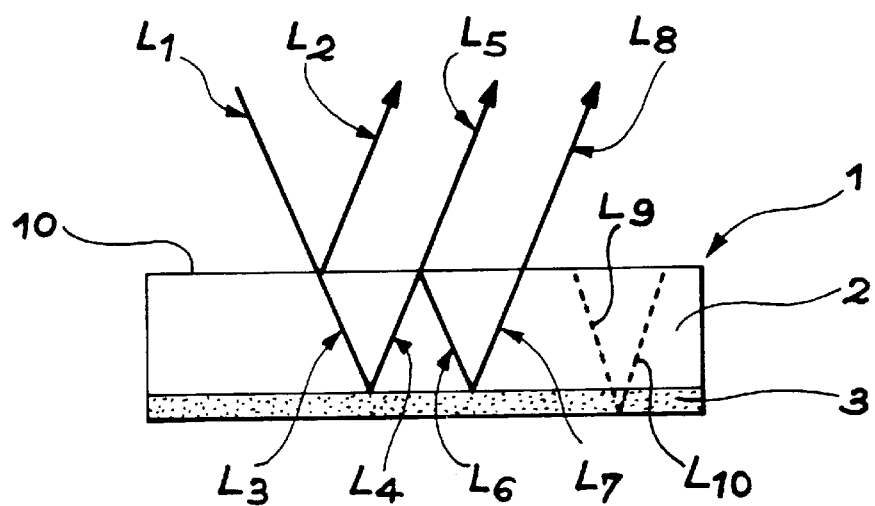
Figure 3:
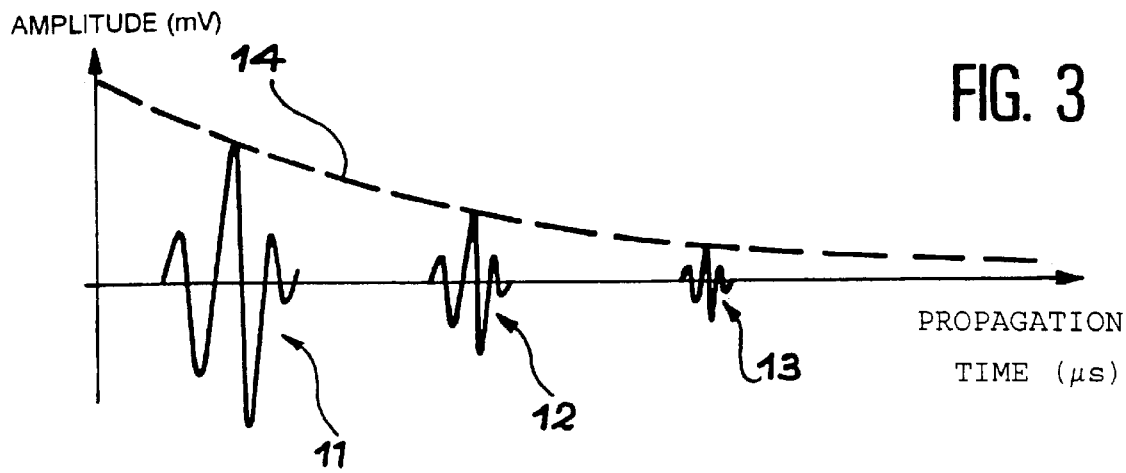
Figure 4:
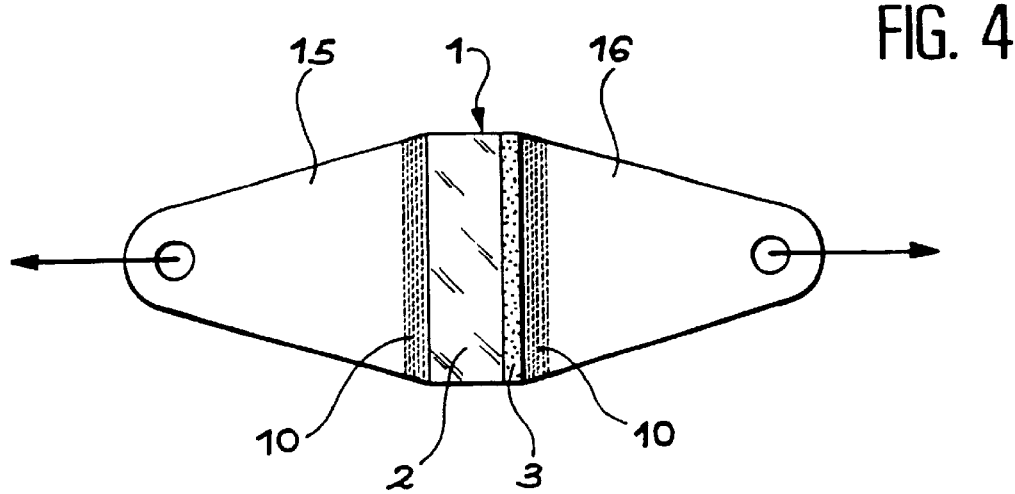
Figure 5:
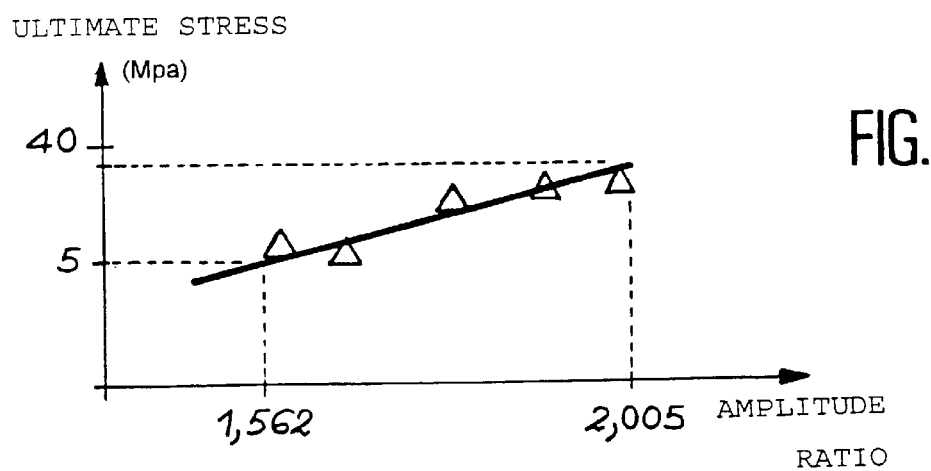

We will now describe the invention with reference to the figures, in which:

FIG. 1 illustrates the equipment used for the method,

FIG. 2 explains the physical phenomena involved in the propagation of ultrasounds, FIG. 3 illustrates a curve of the echoes obtained and an interpretation of this curve, FIG. 4 illustrates a mechanical tear off test, and FIG. 5 shows a correlation between the mechanical tests and ultrasound tests.

FIG. 1 shows that a test piece reference 1 consists of a substrate 2 on which a much thinner coating 3 is deposited by a process such as plasma projection, for which bond measurements are extremely important due to the irregularity and therefore the fragility of the coating structure. Test piece 1 is dipped into water in a tank 4 and is placed on blocks 5 at the bottom of the tank, the coating 3 facing downwards. A sensor 6 is placed above test piece 1, approximately perpendicular to the substrate 2 coating 3 interface, and it is connected to a control means 7 through an oscilloscope 8 and a pulse generator 9. The sensor 6 emits ultrasounds to the test piece 1 and also operates like a receiver; the oscilloscope 8 records the echoes that it receives so that they can be interpreted as will be considered later. As a variant, it would be possible to emit ultrasounds and receive them by separate sensors.

FIG. 2 illustrates one possible phenomenon of ultrasound propagation in test piece 1 in which the direction of the ultrasounds is oblique, unlike what is done in the embodiment in FIG. 1 in which the same sensor emits and receives waves with vertical propagation; this layout was adapted for reasons of clarity in the presentation and to remain general in the description, but the measurement principle remains the same.

Each equipment medium has a particular acoustic impedance. When an acoustic wave reaches the limit of one medium and enters another, one portion penetrates into this other medium and another portion is reflected and returned into the first medium; the proportion of the two portions depends on the impedance of the media, the transmission being 100% when the impedances are equal. As shown in FIG. 2, a wave transmitted by line L1 in the water in tank 4 and that reaches the upper surface 10 opposite the coating 3 of the substrate 2 is partially reflected along line L2 as a first echo, but the remainder of its energy enters substrate 2 along line L3 to reach the interface with the coating 3. Some of this energy is reflected at this point and passes through the substrate 2 in the opposite direction along line L4, and some of it comes out through the top face 10 along line L5 prolonging line L4 forming a second echo. The rest of the energy of the wave along L3 enters the coating 3 and gets lost in it, escaping detection, since the thickness of coating 3 is so thin that it is only possible to pass Lamb waves through it that are oriented in its plane and the attenuation of the waves is very fast in the complex micrographic structures obtained by plasma protection. Part of the wave passing along line L4 is reflected again on the top face 10 of substrate 2, and once again passes through the thickness of substrate 2 along line L6 before some of its energy is once again reflected upwards along line L7 at the substrate 2 coating 3 interface. A third echo is then formed by the portion of energy of the wave that exits from substrate 2 through the top face 10, along line L8 along the continuation of line L7. Successive echoes are produced in the same way and are recorded by sensor 6.

Note that lines L3, L4, L6, L7, etc. passing through substrate 2 are all the same length, such that successive echoes reaching sensor 6 along lines L2, L5, L8, etc., are separated by equal times, corresponding to the time necessary for ultrasounds to pass twice through each of the lengths mentioned above in substrate 2.

The process consists of taking at least three successive echoes of the wave emitted by the sensor 6; they are marked references 11, 12 and 13 on the diagram in FIG. 3, which is a record of the oscilloscope 8; their amplitudes are continuously decreasing and may be evaluated by an envelope curve 14 that has the equation of an exponential.

The parameter of this exponential that is determined as follows may be correlated to the bond of the coating 3. If the amplitude of the wave emitted by sensor 6 is equal to $A_0$, the amplitude of the wave of the first echo ($L_2$) is $A_1 = A_0 r_{10} e^{-2h\alpha}$, where $r_{10}$ is the reflection coefficient of the wave on the top face 10, h is the distance traveled between the top face 10 and the sensor 6, and $\alpha$ is the damping coefficient of ultrasounds in water; The amplitude of the second echo ($L_5$) is $A_2 = A_0 t_{10} t_{01} r_{2-3} e^{-2h\alpha} e^{-2x\beta}$, where $t_{10}$ is the transmission coefficient through the top face 10 of water into the material and $t_{01}$ from the material to water, $r_{2-3}$ is the reflection coefficient at the substrate 2-coating 3 interface, x is the thickness of material 2 and $\beta$ is the damping coefficient in substrate 2; the amplitude of the third echo ($L_8$) is $A_3 = A_0 t_{10} t_{01} r_{2-3}^2 r_{10} e^{-2h\alpha} e^{-4x\beta}$ It can be seen that $\frac{A_3}{A_2} = r_{2-3}r_{10}e^{-2h\alpha}$, and that successive echoes will take place in the same ratio except for the first ($A_1$). It has been seen that this attenuation ratio is representative of the bond of coating 3. The correlation may be set up by preliminary experiments on test pieces for which the attenuation ratio is measured, and the resistance of the coating to tear off is measured successively and directly. When the correlation function has been obtained, the test pieces are then only subjected to the non-destructive ultrasound test.

We have been considering the case of absorption of ultrasound waves in coating 3, only the portions of the wave reflected at the substrate 2-coating 3 interface can return to sensor 6. This is a frequent case since plasma coatings usually have a much lower impedance than metals that could be used to make up substrate 2, such that the coefficient $r_{2-3}$ is high. But exceptions can occur in which the impedances of the coating 3 and the substrate 2 are matched and absorption of waves by thicker coatings 3 is lower. In this case it is found that the echoes no longer come from reflections at the substrate 2-coating 3 interface, but from reflections on the lower face of the coating 3 along lines such as $L_9$ and $L_{10}$. The formula giving the amplitudes of the echoes is then complicated in that the attenuation of the waves in coating 3 has to be included, and the coefficient $[2.(t_{2-3}r_3)]$ replaces $r_{2-3}$, where $t_{2-3}$ is the transmission coefficient at the interface and $r_3$ is the reflection coefficient between the coating 3 and the liquid, but the procedure does not change; a ratio between echoes is calculated and is correlated to a function obtained in advance to estimate the bond of coating 3.

It is remarkable that the position of the test piece 1 does not have any influence on the ratio between echoes that is unchanged if the coating 3 is placed on top, towards sensor 1, but it is preferred to proceed as shown in order to avoid passing through the coating 3 and the consequent absorptions.

The amplitudes of echoes may be defined by an envelope function $A = ke^{-x\Sigma L}$, where k is a constant, $\Sigma L$ is the total length through which the waves pass in the substrate 2 (or more generally in test piece 1), or $(L_3+L_4)$ for the first echo, $(L_3+L_4+L_6+L_7)$ for the second echo, etc., and x is a constant parameter different for each test piece 1 that can be correlated to the bond of coating 3.

The initial search for the correlation function requires mechanical tests on calibration test pieces 1. As mentioned in the beginning, the face 10 of the substrate 2 and the free face of the coating 3 are glued to jaws 15 and 16 that are placed in a tensile testing machine, not shown on FIG. 4, to tear off the coating 3. Tests are carried out on batches composed of several similar test pieces 1, and the highest tear off resistance found in each of these batches is selected. One important item of information that was found is that the highest of these tear off resistance values is probably the most realistic, because they are the only values that can be simply correlated to the ultrasound measurements; other values are possibly the result of initiating failures caused by defective bonding or tension. The correlation found between the tear off stress σ thus obtained and the decay parameter x calculated in advance is linear, and is very good as shown in FIG. 5. The points of the function are determined by varying the conditions of spraying the coating 3 for each test piece batch 1, with an invariable composition of the coating and substrate 2. They were obtained using depositions of alloy KC25NW, type 1, onto Hastelloy X.

The process makes it possible to evaluate the bond on a series of points of test pieces 1 in order to estimate its uniformity.

What is claimed is:

1. Process for measuring a bond of a coating on a substrate, comprising:
    sending ultrasounds into the substrate and into the coating;
    picking up a series of echoes resulting from ultrasound reflections on faces of the substrate with an interface between the substrate and the coating;
    evaluating an echo attenuation coefficient determining a decay in an amplitude of echoes as a function of a number of echo reflections; and
    deducing the bond of a correlation function estimated in advance using calibration test pieces, between attenuation coefficients and values of the bond of the coatings determined by performing mechanical tests on calibration test pieces;
    wherein the correlation function is obtained by manufacturing plural batches of calibration test pieces, the test pieces in each batch being identical, by tearing the coatings off the substrates by tension while measuring tear off resistance for each calibration test piece, and using a best tear off resistance in each of the batches as the resistance to tear off in the correlation function.

2. Process for measuring the bond of a coating on a substrate according to claim 1, wherein the attenuation coefficient is a coefficient of an exponential function that multiplies a distance through which ultrasounds have passed in the test piece.

3. Process for measuring the bond of a coating on a substrate according to claim 2, wherein a single sensor emits and receives the ultrasounds perpendicular to the coating and to the substrate, and the coating is on one face of the test piece remote from the sensor.

4. Process for measuring the bond of a coating on a substrate according to claim 1, wherein a single sensor emits and receives the ultrasounds perpendicular to the coating and to the substrate, and the coating is on one face of the test piece remote from the sensor.

5. Process for measuring the bond of a coating on a substrate, comprising:
    sending ultrasounds into the substrate and to the coating;
    picking up a series of echoes resulting from ultrasound reflections on faces of the substrate, said faces comprising an interface between the substrate and the coating,
    evaluating an echo attenuation coefficient determining a decay in the amplitude of echoes as a function of the number of echo reflections on said interface, and
    deducing the said bond from a correlation function between values of said attenuation coefficients and values of the bond, said correlation function having been determined previously by performing mechanical tests on calibration test pieces.

6. Process for measuring the bond of a coating on a substrate according to claim 5, wherein the correlation function is obtained by manufacturing several batches of calibration test pieces, the test pieces in each batch being identical, by tearing the coatings off the substrates by tension while measuring the tear off resistance for each calibration test piece, and using the best tear off resistance in each of the batches as one value of the bond in the correlation function.

7. Process for measuring the bond of a coating on a substrate according to claim 6, wherein the attenuation coefficient is a coefficient of an exponential function that multiplies a distance through which ultrasounds have passed in the test piece, the exponential function being proportional to the amplitude of the echoes.

8. Process for measuring the bond of a coating on a substrate according to claim 7, wherein a single sensor emits and receives the ultrasounds perpendicular to the coating and to the substrate, and the coating is on one face of the test piece remote from the sensor.

9. Process for measuring the bond of a coating on a substrate according to claim 6, wherein a single sensor emits and receives the ultrasounds perpendicular to the coating and to the substrate, and the coating is on one face of the test piece remote from the sensor.

10. Process for measuring the bond of a coating on a substrate according to claim 5, wherein the attenuation coefficient is a coefficient of an exponential function that multiplies a distance through which ultrasounds have passed in the test piece, the exponential function being proportional to the amplitude of the echoes.

11. Process for measuring the bond of a coating on a substrate according to to claim 10, wherein a single sensor emits and receives the ultrasounds perpendicular to the coating and to the substrate, and the coating is on one face of the test piece remote from the sensor.

12. Process for measuring the bond of a coating on a substrate according to claim 5, wherein a single sensor emits and receives the ultrasounds perpendicular to the coating and to the substrate, and the coating is on one face of the test piece remote from the sensor.

* * * * *